(12) United States Patent
Pinkel et al.

(10) Patent No.: US 7,267,947 B2
(45) Date of Patent: *Sep. 11, 2007

(54) ARRAY-BASED DETECTION OF GENETIC ALTERATIONS ASSOCIATED WITH DISEASE

(75) Inventors: Daniel Pinkel, Walnut Creek, CA (US); Donna G. Albertson, Lafayette, CA (US); Joe W. Gray, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 496 days.

This patent is subject to a terminal disclaimer.

(21) Appl. No.: 10/198,805

(22) Filed: Jul. 19, 2002

(65) Prior Publication Data

US 2002/0192698 A1     Dec. 19, 2002

Related U.S. Application Data

(63) Continuation of application No. 09/577,688, filed on May 22, 2000, now abandoned, which is a continuation of application No. 08/908,855, filed on Aug. 8, 1997, now Pat. No. 6,210,878.

(51) Int. Cl.
*C12Q 1/68*     (2006.01)
(52) U.S. Cl. ............... 435/6; 435/40.5; 435/40.52
(58) Field of Classification Search ............... 435/6, 435/40.5, 40.52
See application file for complete search history.

(56) References Cited

U.S. PATENT DOCUMENTS 5,472,842 A * 12/1995 Stokke et al. ............... 435/6

FOREIGN PATENT DOCUMENTS

| WO | WO95/09929 A1 * | 4/1995 |
| WO | WO96/17958 A | 6/1996 |
| WO | WO97/14811 A | 4/1997 |
| WO | WO98/02539 | 1/1998 |

OTHER PUBLICATIONS

A. Kallioniemi et al., *Science* (1992) 258:818-821.
T. Sato et al., *Cancer Research* (1990) 50:7184-7189.
M. M. Tanner et al., *Cancer Research* (1996) 56:3441-3445.
M. M. Tanner et al., *Cancer Research* (1994) 54:4257-4260.
Hollings, P.E., "Molecular heterogeneity at the breakpoints of smaller 20q deletions," *Genes, Chromosomes & Cancer*, Sep. 1994, vol. 11, No. 1, pp. 21-28.
James, L.A., et al., "Comparative genomic hybridization of ductal carcinoma in situ of the breast: identification of regions of DNA amplification and deletion in common with invasive breast carcinoma," *Oncogene*, Mar. 6, 1997, vol. 14, No. 9, pp. 1059-1065.
Keith, W.N., et al., "Co-amplification of erbB2, topoisomerase II alpha and retinoic acid receptor alpha genes in breast cancer and allelic loss at topoisomerase I on chromosome 20," *European Journal of Cancer*, 1993, vol. 29A, No. 10, pp. 1469-1475.
Pinkel, D., et al., "High resolution analysis of DNA copy number variation using comparative genomic hybridization to microarrays," *Nature Genetics*, Oct. 1998, vol. 20, pp. 207-211.
Webster, M.A., et al., "Induction of mammary epithelial hyperplasias and mammary tumors in transgenic mice expressing a murine mammary tumor virus/activated c-src fusion gene," *Proceedings of the National Academy of Sciences of the United States of America*, Aug. 15, 1995, vol. 92, No. 17, pp. 7849-7853.

\* cited by examiner

*Primary Examiner*—Mark L. Shibuya
(74) *Attorney, Agent, or Firm*—Townsend and Townsend and Crew LLP (57) ABSTRACT

The present invention relates to DNA sequences from regions of copy number change on chromosome 20. The sequences can be used in hybridization methods for the identification of chromosomal abnormalities associated with various diseases.

14 Claims, 5 Drawing Sheets

ARRAY-BASED DETECTION OF GENETIC ALTERATIONS ASSOCIATED WITH DISEASE

CROSS-REFERENCE TO RELATED APPLICATIONS

This application is a continuation of U.S. application Ser. No. 09/577,688, filed May 22, 2000 now abandoned, which is a continuation of U.S. application Ser. No. 08/908,855, filed Aug. 8, 1997, now U.S. Pat. No. 6,210,878. This application is also related to U.S. Ser. No. 08/353,018 filed on Dec. 9, 1994. Each application is incorporated herein by reference for all purposes.

STATEMENT AS TO RIGHTS TO INVENTIONS MADE UNDER FEDERALLY SPONSORED RESEARCH OR DEVELOPMENT

This invention was made with Government support under Grant Nos. DE-AC-03-76SF00098 & DE-AC-03-79SF00098, awarded by the Dept. of Energy; CA58207, awarded by the National Institutes of Health; 94-05-0021, awarded by the National Inst. Standards Tech. The Government has certain rights in this invention.

FIELD OF THE INVENTION

This invention pertains to the field of cancer genetics. More particularly this invention pertains to the identification of regions of copy number increase or decrease associated with cancers and other disease.

BACKGROUND OF THE INVENTION

Chromosome abnormalities are often associated with genetic disorders, degenerative diseases, and cancer. In particular, the deletion or multiplication of copies of whole chromosomes or chromosomal segments, and higher level amplifications of specific regions of the genome are common occurrences in cancer. See; for example Smith, et al., *Breast Cancer Res. Treat.*, 18: Suppl. 1: 5-14 (1991, van de Vijer & Nusse, *Biochim. Biophys. Acta.* 1072: 33-50 (1991), Sato, et al., *Cancer. Res.*, 50: 7184-7189 (1990). In fact, the amplification and deletion of DNA sequences containing proto-oncogenes and tumor-suppressor genes, respectively, are frequently characteristic of tumorigenesis. Dutrillaux, et al., *Cancer Genet. Cytogenet.*, 49: 203-217 (1990). Clearly, the identification of such regions and the cloning of the genes involved is crucial both to the study of tumorigenesis and to the development of cancer diagnostics.

The detection of chromosomal regions of increased or decreased copy number has traditionally been done by cytogenetics. Because of the complex packing of DNA into the chromosomes, resolution of cytogenetic techniques has been limited to regions larger than about 10 Mb; approximately the width of a band in Giemsa-stained chromosomes. In complex karyotypes with multiple translocations and other genetic changes, traditional cytogenetic analysis is of little utility because karyotype information is lacking or cannot be interpreted. Teyssier, J. R., *Cancer Genet. Cytogenet.*, 37: 103 (1989). Furthermore, conventional cytogenetic banding analysis is time consuming, labor intensive, and frequently difficult or impossible.

More recently, cloned probes have been used to assess the amount of a given DNA sequence in a chromosome by Southern blotting. This method is effective even if the genome is heavily rearranged so as to eliminate useful karyotype information. However, Southern blotting only gives a rough estimate of the copy number of a DNA sequence, and does not give any information about the localization of that sequence within the chromosome.

Comparative genomic hybridization (CGH) is a more recent approach to identify the presence and localization of amplified/deleted sequences. See Kallioniemi, et al., *Science*, 258: 818 (1992). CGH, like Southern blotting, reveals amplifications and deletions irrespective of genome rearrangement. Additionally, CGH provides a more quantitative estimate of copy number than Southern blotting, and moreover also provides information of the localization of the amplified or deleted sequence in the normal chromosome.

SUMMARY OF THE INVENTION

The present invention relates to the identification of new regions of copy number change on chromosome 20. Nucleic acids specific to these regions are useful as probes or as probe targets for monitoring the relative copy number of corresponding sequences from a biological sample such as a tumor cell.

Thus, in one embodiment, this invention provides methods of detecting a chromosome alteration (e.g., copy number increase or decrease) at about the following FLpter positions: 0.603, 0.646, and 0.675 (all decrease), 0.694 and 0.722 (both increase), and 0.867 (increase). The methods involve contacting a nucleic acid sample from a patient with nucleic acid probes each of which binds selectively to a target regions noted above under conditions in which the probe forms a stable hybridization complex with the target sequence; and detecting the hybridization complex. The step of detecting the hybridization complex can involve determining the copy number of the target sequence. The probe preferably comprises a nucleic acid that specifically hybridizes under stringent conditions to a nucleic acid selected from the probes disclosed here. The probe or the sample nucleic acid can be labeled, and is more typically fluorescently labeled. If the sample is labeled, the probes can be attached to a solid surface as an array.

The probes disclosed here can be used in kits for the detection of a chromosomal abnormality at the positions on human chromosome 20 noted above. The kits include a compartment which contains a labeled nucleic acid probe which binds selectively to a target polynucleotide sequence on human chromosome 20. The probe preferably includes at least one nucleic acid that specifically hybridizes under stringent conditions to a nucleic acid selected from the nucleic acids disclosed here. The kit may further include a reference probe specific to a sequence in the centromere of chromosome 20 or other reference locations.

Definitions

A "nucleic acid sample" as used herein refers to a sample comprising DNA in a form suitable for hybridization to a probes of the invention. The nucleic acid may be total genomic DNA, total mRNA, genomic DNA or mRNA from particular chromosomes, or selected sequences (e.g. particular promoters, genes, amplification or restriction fragments, cDNA, etc.) within particular amplicons or deletions disclosed here. The nucleic acid sample may be extracted from particular cells or tissues. The tissue sample from which the nucleic acid sample is prepared is typically taken from a patient suspected of having the disease associated with the amplification or deletion being detected. In some cases, the nucleic acids may be amplified using standard techniques such as PCR, prior to the hybridization. The sample may be isolated nucleic acids immobilized on a solid surface (e.g., nitrocellulose) for use in Southern or dot blot hybridizations and the like. The sample may also be prepared such that individual nucleic acids remain substantially intact and comprises interphase nuclei prepared according to standard techniques. A nucleic acid sample as used herein may also refer to a substantially intact condensed chromosome (e.g. a metaphase chromosome). Such a condensed chromosome is suitable for use as a hybridization target in in situ hybridization techniques (e.g. FISH). The particular usage of the term "nucleic acid sample" (whether as extracted nucleic acid or intact metaphase chromosome) will be readily apparent to one of skill in the art from the context in which the term is used. For instance, the nucleic acid sample can be a tissue or cell sample prepared for standard in situ hybridization methods described below. The sample is prepared such that individual chromosomes remain substantially intact and typically comprises metaphase spreads or interphase nuclei prepared according to standard techniques.

A "chromosome sample" as used herein refers to a tissue or cell sample prepared for standard in situ hybridization methods described below. The sample is prepared such that individual chromosomes remain substantially intact and typically comprises metaphase spreads or interphase nuclei prepared according to standard techniques.

As used herein, a "nucleic acid array" is a plurality of target elements, each comprising one or more target nucleic acid molecules immobilized on a solid surface to which probe nucleic acids are hybridized. Target nucleic acids of some target elements typically are from regions of copy number change from chromosome 20. The target nucleic acids of a target element may, for example, contain sequence from specific genes or clones disclosed here. Other target elements will contain, for instance, reference sequences. Target elements of various dimensions can be used in the arrays of the invention. Generally, smaller, target elements are preferred. Typically, a target element will be less than about 1 cm in diameter. Generally element sizes are from 1 µm to about 3 mm, preferably between about 5 µm and about 1 mm.

The target elements of the arrays may be arranged on the solid surface at different densities. The target element densities will depend upon a number of factors, such as the nature of the label, the solid support, and the like. One of skill will recognize that each target element may comprise a mixture of target nucleic acids of different lengths and sequences. Thus, for example, a target element may contain more than one copy of a cloned piece of DNA, and each copy may be broken into fragments of different lengths. The length and complexity of the target sequences of the invention is not critical to the invention. One of skill can adjust these factors to provide optimum hybridization and signal production for a given hybridization procedure, and to provide the required resolution among different genes or genomic locations. Typically, the target sequences will have a complexity between about 1 kb and about 1 Mb, sometimes 10 kb and about 500 kb, and usually from about 50 kb to about 150 kb.

The term "nucleic acid" refers to deoxyribonucleotides or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences and as well as the sequence explicitly indicated The phrases "hybridizing specifically to" or "specific hybridization" or "selectively hybridize to", refer to the binding, duplexing, or hybridizing of a nucleic acid molecule preferentially to a particular nucleotide sequence under stringent conditions when that sequence is present in a complex mixture (e.g., total cellular) DNA or RNA.

The term "stringent conditions" refers to conditions under which a probe will hybridize preferentially to its target subsequence, and to a lesser extent to, or not at all to, other sequences. A "stringent hybridization" and "stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993) *Laboratory Techniques in Biochemistry and Molecular Biology—Hybridization with Nucleic Acid Probes* part I chapter 2. Overview of principles of hybridization and the strategy of nucleic acid probe assays, Elsevier, N.Y. Generally, highly stringent hybridization and wash conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Very stringent conditions are selected to be equal to the $T_m$ for a particular probe.

An example of stringent hybridization conditions for hybridization of complementary nucleic acids which have more than 100 complementary residues on a filter in a Southern or northern blot is 42° C. using standard hybridization solutions, with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook et al. (1989) *Molecular Cloning: A Laboratory Manual* (2nd ed.) Vol. 1-3, Cold Spring Harbor Laboratory, Cold Spring Harbor Press, N.Y., (Sambrook et at) supra for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes.

An "isolated" polynucleotide is a polynucleotide which is substantially separated from other contaminants that naturally accompany it, e.g., protein, lipids, and other polynucleotide sequences. The term embraces polynucleotide sequences which have been removed or purified from their naturally-occurring environment or clone library, and include recombinant or cloned DNA isolates and chemically synthesized analogues or analogues biologically synthesized by heterologous systems.

"Subsequence" refers to a sequence of nucleic acids that comprise a part of a longer sequence of nucleic acids.

A "probe" or a "nucleic acid probe", as used herein, is defined to be a collection of one or more nucleic acid fragments whose hybridization to a target can be detected. The probe may be unlabeled or labeled as described below so that its binding to the target can be detected. The probe is produced from a source of nucleic acids from one or more particular (preselected) portions of the genome, for example one or more clones, an isolated whole chromosome or chromosome fragment, or a collection of polymerase chain reaction (PCR) amplification products. The probes of the present invention are produced from nucleic acids found in the regions described herein. The probe may be processed in some manner, for example, by blocking or removal of repetitive nucleic acids or enrichment with unique nucleic acids. Thus the word "probe" may be used herein to refer not only to the detectable nucleic acids, but to the detectable nucleic acids in the form in which they are applied to the target, for example, with the blocking nucleic acids, etc. The blocking nucleic acid may also be referred to separately. What "probe" refers to specifically is clear from the context in which the word is used.

The probe may also be isolated nucleic acids immobilized on a solid surface (e.g., nitrocellulose). In some embodiments, the probe may be a member of an array of nucleic acids as described, for instance, in WO 96/17958. Techniques capable of producing high density arrays can also be used for this purpose (see, e.g., Fodor et al. *Science* 767-773 (1991) and U.S. Pat. No. 5,143,854).

"Hybridizing" refers to the binding of two single stranded nucleic acids via complementary base pairing.

One of skill will recognize that the precise sequence of the particular probes described herein can be modified to a certain degree to produce probes that are "substantially identical" to the disclosed probes, but retain the ability to bind substantially to the target sequences. Such modifications are specifically covered by reference to the individual probes herein. The term "substantial identity" of polynucleotide sequences means that a polynucleotide comprises a sequence that has at least 90% sequence identity, more preferably at least 95%, compared to a reference sequence using the methods described below using standard parameters.

Two nucleic acid sequences are said to be "identical" if the sequence of nucleotides in the two sequences is the same when aligned for maximum correspondence as described below. The term "complementary to" is used herein to mean that the complementary sequence is identical to all or a portion of a reference polynucleotide sequence.

DETAILED DESCRIPTION

The present invention provides new regions of copy number changes on human chromosome 20. The clones and other information provided herein can be used to detect the copy number changes in a biological sample and thereby screen for the presence of disease, such as breast cancer. Generally the methods involve hybridization of probes that specifically bind one or more nucleic acid sequences of the target region with nucleic acids present in a biological sample or derived from a biological sample. The locations of particular chromosomal regions and/or target regions for particular probes are typically expressed as the average fractional length from the p telomere (FLpter).

As used herein, a biological sample is a sample of biological tissue or fluid containing cells desired to be screened for chromosomal abnormalities (e.g. amplifications or deletions). In a preferred embodiment, the biological sample is a cell or tissue suspected of being cancerous (transformed). Methods of isolating biological samples are well known to those of skill in the art and include, but are not limited to, aspirations, tissue sections, needle biopsies, and the like. Frequently the sample will be a "clinical sample" which is a sample derived from a patient. Biological samples may also include sections of tissues such as frozen sections or parafin sections taken for histological purposes. It will be recognized that the term "sample" also includes supernatant (containing cells) or the cells themselves from cell cultures, cells from tissue culture and other media in which it may be desirable to detect chromosomal abnormalities.

In some embodiments, a chromosome sample is prepared by depositing cells, either as single cell suspensions or as tissue preparation, on solid supports such as glass slides and fixed by choosing a fixative which provides the best spatial resolution of the cells and the optimal hybridization efficiency. In other embodiments, the sample is contacted with an array of probes immobilized on a solid surface.

Making Probes

Any probe which hybridizes to regions of altered copy number are suitable for use in detecting the corresponding regions. Methods of preparing probes are well known to those of skill in the art (see, e.g Sambrook et al., *Molecular Cloning: A Laboratory Manual* (2nd ed), Vols. 1-3, Cold Spring Harbor Laboratory, (1989) or *Current Protocols in Molecular Biology*, F. Ausubel et al., ed. Greene Publishing and Wiley-Interscience, New York(1987))

Given the strategy for making the nucleic acids of the present invention, one of skill can construct a variety of vectors and nucleic acid clones containing functionally equivalent nucleic acids to the particular probes disclosed here. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology* volume 152 Academic Press, Inc., San Diego, Calif. (Berger); Sambrook et al. (1989) *Molecular Cloning—A Laboratory Manual* (2nd ed.) Vol. 1-3, Cold Spring Harbor Laboratory, Cold Spring Harbor Press, N.Y., (Sambrook); and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

The nucleic acids provided by this invention, whether RNA, cDNA, genomic DNA, or a hybrid of the various combinations, are isolated from biological sources or synthesized in vitro. The nucleic acids and vectors of the invention are present in transformed or transfected whole cells, in transformed or transfected cell lysates, or in a partially purified or substantially pure form.

In vitro amplification techniques suitable for amplifying sequences to provide a nucleic acid, or for subsequent analysis, sequencing or subcloning are known. Examples of techniques sufficient to direct persons of skill through such in vitro amplification methods, including random priming, the polymerase chain reaction (PCR) the ligase chain reaction (LCR), Qβ-replicase amplification and other RNA polymerase mediated techniques (e.g., NASBA) are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47; *The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al (1990) *Gene* 89, 117, and Sooknanan and Malek (1995) *Biotechnology* 13: 563-564. Improved methods of cloning in vitro amplified nucleic acids are described in Wallace et al., U.S. Pat. No. 5,426,039. Improved methods of amplifying large nucleic acids are summarized in Cheng et al (1994) *Nature* 369: 684-685 and the references therein.

Nucleic Acids (e.g., oligonucleotides) for in vitro amplification methods or for use as gene probes, for example, are typically chemically synthesized according to the solid phase phosphoramidite triester method described by Beaucage and Caruthers (1981), *Tetrahedron Letts.*, 22(20):1859-1862, e.g., using an automated synthesizer, as described in Needham-VanDevanter et al (1984) *Nucleic Acids Res.,* 12:6159-6168. Purification of oligonucleotides, where necessary, is typically performed by either native acrylamide gel electrophoresis or by anion-exchange HPLC as described in Pearson and Regnier (1983) *J. Chrom.* 255:137-149. The sequence of the synthetic oligonucleotides can be verified using the chemical degradation method of Maxam and Gilbert (1980) in Grossman and Moldave (eds.) Academic Press, New York, *Methods in Enzymology* 65:499-560.

The probes are most easily prepared by combining and labeling one or more of the clones disclosed here. Prior to use, the constructs are fragmented to provide smaller nucleic acid fragments that easily penetrate the cell and hybridize to the target nucleic acid. Fragmentation can be by any of a number of methods well known to hose of skill in the art. Preferred methods include treatment with a restriction enzyme to selectively cleave the molecules, or alternatively to briefly heat the nucleic acids in the presence of $Mg^{2+}$. Probes are preferably fragmented to an average fragment length ranging from about 50 bp to about 2000 bp, more preferably from about 100 bp to about 1000 bp and most preferably from about 150 bp to about 500 bp.

One of skill will appreciate that using the clones provided herein, one of skill in the art can identify or isolate the same or similar probes from other human genomic libraries using routine methods (e.g. by STS content, Southern or Northern Blots).

Labeling Nucleic Acids

Methods of labeling nucleic acids (either probes or sample nucleic acids) are well known to those of skill in the art. Preferred labeled labels are those that are suitable for use in in situ hybridization. The nucleic acid probes or samples of the invention may be detectably labeled prior to the hybridization reaction. Alternatively, a detectable label which binds to the hybridization product may be used. Such detectable labels include any material having a detectable physical or chemical property and have been well-developed in the field of immunoassays.

As used herein, a "label" is any composition detectable by spectroscopic, photochemical, biochemical, immunochemical, or chemical means. Useful labels in the present invention include radioactive labels (e.g. $^{32}P$, $^{125}I$, $^{14}C$, $^{3}H$, and $^{35}S$), fluorescent dyes (e.g. fluorescein, rhodamine, Texas Red, etc.), electron-dense reagents (e.g. gold), enzymes (as commonly used in an ELISA), colorimetric labels (e.g. colloidal gold), magnetic labels (e.g. Dynabeads™), and the like. Examples of labels which are not directly detected but are detected through the use of directly detectable label include biotin and dioxigenin as well as haptens and proteins for which labeled antisera or monoclonal antibodies are available.

The particular label used is not critical to the present invention, so long as it does not interfere with the in situ hybridization of the probe. However, probes directly labeled with fluorescent labels (e.g. fluorescein-12-dUTP, Texas Red-5-dUTP, etc.) are preferred for chromosome hybridization.

A direct labeled probe, as used herein, is a probe to which a detectable label is attached. Because the direct label is already attached to the probe, no subsequent steps are required to associate the probe with the detectable label. In contrast, an indirect labeled probe is one which bears a moiety to which a detectable label is subsequently bound, typically after the probe is hybridized with the target nucleic acid.

In addition the label must be detectible in as low copy number as possible thereby maximizing the sensitivity of the assay and yet be detectible above any background signal. Finally, a label must be chosen that provides a highly localized signal thereby providing a high degree of spatial resolution when physically mapping the stain against the chromosome. Particularly preferred fluorescent labels include fluorescein-12-dUTP and Texas Red-5-dUTP.

The labels may be coupled to the probes in a variety of means known to those of skill in the art. In a preferred embodiment the nucleic acid probes will be labeled using nick translation, PCR, or random primer extension (Rigby, et al. *J. Mol. Biol.*, 113: 237 (1977) or Sambrook, et al., *Molecular Cloning—A Laboratory Manual*, Cold Spring Harbor Laboratory, Cold Spring Harbor, N.Y. (1985)).

Detecting the Regions Disclosed Here

As explained above, detection of copy number changes in chromosome 20 is indicative of the presence and/or prognosis of a large number of cancers. These include, but are not limited to breast, prostate, cervix, ovary, bladder, head and neck, and colon.

In a preferred embodiment, the copy number changes are detected through the hybridization of a probe of this invention to a target nucleic acid (e.g. a chromosomal sample) in which it is desired to screen for the amplification or deletion. Suitable hybridization formats are well known to those of skill in the art and include, but are not limited to, variations of Southern Blots, in situ hybridization and quantitative amplification methods such as quantitative PCR (see, e.g. Sambrook, supra., Kallioniemi et al., *Proc. Natl Acad Sci*

USA, 89: 5321-5325 (1992), and *PCR Protocols, A Guide to Methods and Applications*, Innis et al., Academic Press, Inc. N.Y., (1990)).

Alternatively, binding to a target nucleic acid can be compared between a "test" nucleic acid and a "reference" nucleic acid. Preferred sources for "test" nucleic acids include any organism, organ, tissue, or cell type in whose DNA it is desirable to identify a chromosomal abnormality. The "reference" nucleic acid is typically total genomic DNA from a normal cell and should not include the copy number changes that are the target it is desired to detect. Hybridization to a particular target sequence is then compared as described in the Example Section below.

In situ Hybridization,

In some embodiments, the target region is identified using in situ hybridization. Generally, in situ hybridization comprises the following major steps: (1) fixation of tissue or biological structure to analyzed; (2) prehybridization treatment of the biological structure to increase accessibility of target DNA, and to reduce nonspecific binding; (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments. The reagent used in each of these steps and their conditions for use vary depending on the particular application.

In some applications it is necessary to block the hybridization capacity of repetitive sequences. In this case, human genomic DNA or Cot1 DNA, is used as an agent to block such hybridization. The preferred size range is from about 200 bp to about 1000 bases, more preferably between about 400 to about 800 bp for double stranded, nick translated nucleic acids.

Hybridization protocols for the particular applications disclosed here are described in Pinkel et al. *Proc. Natl. Acad. Sci. USA*, 85: 9138-9142 (1988) and in EPO Pub. No. 430,402. Suitable hybridization protocols can also be found in *Methods o\in Molecular Biology Vol. 33: In Situ Hybridization Protocols*, K. H. A. Choo, ed., Humana Press, Totowa, N.J., (1994). In a particularly preferred embodiment, the hybridization protocol of Kallioniemi et al., *Proc. Natl Acad Sci USA*, 89: 5321-5325 (1992) is used.

Typically, it is desirable to use dual color FISH, in which two probes are utilized, each labeled by a different fluorescent dye. A test probe that hybridizes to the region of interest is labeled with one dye, and a control probe that hybridizes to a different region (e.g., a centromere) is labeled with a second dye. A nucleic acid that hybridizes to a stable portion of the chromosome of interest, or another chromosome, is often most useful as the control probe. In this way, differences between efficiency of hybridization from sample to sample can be accounted for.

The FISH methods for detecting chromosomal abnormalities can be performed on nanogram quantities of the subject nucleic acids. Paraffin embedded tumor sections can be used, as can fresh or frozen material. Because FISH can be applied to the limited material, touch preparations prepared from uncultured primary tumors can also be used (see, e.g., Kallioniemi, A. et al., *Cytogenet. Cell Genet*. 60: 190-193 (1992)). For instance, small biopsy tissue samples from tumors can be used for touch preparations (see, e.g., Kallioniemi, A. et al., *Cytogenet. Cell Genet*. 60: 190-193 (1992)). Small numbers of cells obtained from aspiration biopsy or cells in bodily fluids (e.g., blood, urine, sputum and the like) can also be analyzed. For prenatal diagnosis, appropriate samples will include amniotic fluid and the like.

Arrays

Other formats use arrays of probes or targets to which nucleic acid samples are hybridized as described below and in WO 96/17958. The array nucleic acids preferably include nucleic acids selected from a particular region of copy number change disclosed here. Typically, the array nucleic acids will include nucleic aid molecules derived from representative locations along the chromosomal region of interest, a cDNA library, and the like. These target nucleic acids may be relatively long (typically thousands of bases) fragments of nucleic acid obtained from, for instance, genomic clones, inter-Alu PCR products of genomic clones, restriction digests of genomic clone, cDNA clones and the like. In preferred embodiments the array nucleic acids are a previously mapped library of clones spanning a particular region of interest. The arrays can be used with a single population of sample nucleic acids or can be used with two differentially labeled collections, as described below.

Many methods for immobilizing nucleic acids on a variety of solid surfaces are known in the art. For instance, the solid surface may be a membrane, glass, plastic, or a bead. The desired component may be covalently bound or non-covalently attached through nonspecific binding. The immobilization of nucleic acids on solid surfaces is discussed more fully below.

A wide variety of organic and inorganic polymers, as well as other materials, both natural and synthetic, may be employed as the material for the solid surface. Illustrative solid surfaces include nitrocellulose, nylon, glass, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition substances that form gels can be used. Such materials include proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like.

If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature. For example, methods for immobilizing nucleic acids by introduction of various functional groups to the molecules is known (see, e.g., Bischoff et al. (1987) *Anal. Biochem.*, 164:336-344; Kremsky et al. (1987) *Nucl. Acids Res*. 15:2891-2910). Modified nucleotides can be placed on the target using PCR primers containing the modified nucleotide, or by enzymatic end labeling with modified nucleotides.

Use of membrane supports (e.g., nitrocellulose, nylon, polypropylene) for the nucleic acid arrays of the invention is advantageous because of well developed technology employing manual and robotic methods of arraying targets at relatively high element densities. Such membranes are generally available and protocols and equipment for hybridization to membranes is well known. Many membrane materials, however, have considerable fluorescence emission, where fluorescent labels are used to detect hybridization.

To optimize a given assay format one of skill can determine sensitivity of fluorescence detection for different combinations of membrane type, fluorochrome, excitation and emission bands, spot size and the like. In addition, low fluorescence background membranes have been described (see, e.g., Chu et al. (1992) *Electrophoresis* 13:105-114).

The sensitivity for detection of spots of various diameters on the candidate membranes can be readily determined by, for example, spotting a dilution series of fluorescently end labeled DNA fragments. These spots are then imaged using conventional fluorescence microscopy. The sensitivity, linearity, and dynamic range achievable from the various combinations of fluorochrome and membranes can thus be determined. Serial dilutions of pairs of fluorochrome in known relative proportions can also be analyzed to determine the accuracy with which fluorescence ratio measurements reflect actual fluorochrome ratios over the dynamic range permitted by the detectors and membrane fluorescence.

Arrays on substrates with much lower fluorescence than membranes, such as glass, quartz, or small beads, can achieve much better sensitivity. For example, elements of various sizes, ranging from 1 mm diameter down to 1 µm can be used with these materials. Small array members containing small amounts of concentrated target DNA are conveniently used for high complexity comparative hybridizations since the total amount of probe available for binding to each element will be limited. Thus it is advantageous to have small array members that contain a small amount of concentrated target DNA so that the signal that is obtained is highly localized and bright. Such small array members are typically used in arrays with densities greater than $10^4/cm^2$. Relatively simple approaches capable of quantitative fluorescent imaging of 1 cm2 areas have been described that permit acquisition of data from a large number of members in a single image (see, e.g., Wittrup et. al. (1994) *Cytometry* 16:206-213).

Substrates such as glass or fused silica are advantageous in that they provide a very low fluorescence substrate, and a highly efficient hybridization environment. Covalent attachment of the target nucleic acids to glass or synthetic fused silica can be accomplished according to a number of known techniques. Nucleic acids can be conveniently coupled to glass using commercially available reagents. For instance, materials for preparation of silanized glass with a number of functional groups are commercially available or can be prepared using standard techniques (see, e.g., Gait et al. (1984) Oligonucleotide Synthesis: A Practical Approach, IRL Press, Washington, D.C.). Similarly, quartz cover slips, which have at least 10-fold lower auto fluorescence than glass, can also be silanized.

The targets can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith et al. (1992) *Science*, 258:1122-1126). Biotin or digoxigenin end-labeled nucleic acids can be prepared according to standard techniques.

Hybridization to nucleic acids attached to beads is accomplished by suspending them in the hybridization mix, and then depositing them on the glass substrate for analysis after washing. Alternatively, paramagnetic particles, such as ferric oxide particles, with or without avidin coating, can be used.

In one particularly preferred embodiment, the target elements are spotted onto a surface (e.g., a glass or quartz surface). The targets can be made by dissolving the nucleic acid in a mixture of dimethylsulfoxide (DMSO), and nitrocellulose and spotting the mixture onto amino-silane coated glass slides with small capillaries, as described below.

Other Formats

A number of hybridization formats are useful in the invention. For instance, Southern hybridizations can be used. In a Southern Blot, a genomic or cDNA (typically fragmented and separated on an electrophoretic gel) is hybridized to a probe specific for the target region. Comparison of the intensity of the hybridization signal from the probe for the target region with the signal from a probe directed to a control (non amplified) region provides an estimate of the relative copy number of the target nucleic acid.

Kits Containing Probes,

This invention also provides diagnostic kits for the detection of chromosomal abnormalities on chromosome 20. In a preferred embodiment, the kits include one or more probes to the regions disclosed here. The kits can additionally include blocking probes and instructional materials describing how to use the kit contents in detecting the target regions. The kits may also include one or more of the following: various labels or labeling agents to facilitate the detection of the probes, reagents for the hybridization including buffers, a metaphase spread, bovine serum albumin (BSA) and other blocking agents, tRNA, SDS sampling devices including fine needles, swabs, aspirators and the like, positive and negative hybridization controls and so forth.

EXAMPLES

The following examples are offered to illustrate, but not to limit the present invention.

In this example we describe a new implementation of CGH that employs microarrays of mapped genomic DNA clones in place of metaphase chromosomes as the hybridization target. This approach improves the resolution by more that a factor of 100 and references the results to the genetic maps being produced by the Human Genome Project. We have demonstrated the power of this approach through a multi-locus analysis of copy number changes on chromosome 20 in breast cancer. Three new independent regions of copy number change were resolved in a portion of a chromosome that had previously been extensively studied, and the boundaries of one region were mapped to within the length of a clone.

Methods

Arrays: Cloned DNA was isolated from bacterial cultures using standard procedures. Ten µg of each DNA was ethanol precipitated and dissolved first in 1 µl of water. Four µl of a solution of nitrocellulose filter material dissolved in DMSO (0.5 µg/µl) was added and mixed. The solution was lightly sonicated to reduce the fragment size to several kb so that it is not too stringy for effective spotting. Sub-nanoliter amounts of each target solution were deposited using a glass capillary onto an acidcleaned, amino propyltrimethoxysilane glass or quartz surface, and air dried. Final spot diameters were 150-250 µm.

Hybridization: Test and reference genomic DNA were labeled by nick translation with fluorescein dCTP and Texas red dCTP respectively. Two hundred to 400 ng of each were mixed with 50 µg of Cot-1 DNA and ethanol precipitated. The amount of Cot-1 DNA was based on fluorimetric determination since absorbance measurements of some commercial preparations substantially overestimate the concentration of effective DNA that they contain. This DNA was dissolved in 10 µl of hybridization mix to achieve a final composition of 50% formamide/ 10% dextran sulfate/2×SSC/2% SDS and 100 µg tRNA. The DNA was denatured at 70° C. for 5 minutes, and incubated at 37° C. for several hours to allow blocking of the repetitive sequences. A well enclosing ~1 cm² around the perimeter of the array was filled with the reassociated hybridization mix (10 µl/cm² of surface), and the array was placed in a sealed tube (containing 100 µl of hybridization solution without probe to prevent evaporation) at 37° C. for 16-60 hrs on slowly rocking table to actively transport the hybridization mix over the array. After hybridization the slide was washed in 50% formamide/ 2×SSC at 45° C. for 10 minutes, followed by phosphate buffer containing 0.05% NP40 and antifade solution containing 1 µg/ml of DAPI to counter stain the array targets was applied, and a glass coverslip sealed in place.

Fluorescence Imaging and Analysis: Fluorescence images of 5 mm×7 mm regions of the array were obtained using a 1× magnification imaging system coupled to a 12 bit CCD camera (Photometrics KAF 1400 chip). Excitation light, supplied from a mercury arc lamp equipped with a computer controlled filter wheel, was coupled into the back of the slide using a quartz prism. After passing through the array elements it underwent total internal reflection from the outside surface of the cover slip, passed back through the specimen and into a mirror, and was reflected back to the specimen by a fixed mirror. A multiband pass filter (P8100, Chroma Technology, Brattleboro Vt.) was used in the emission light path. Exposure times were much less than one second for DAPI, and between 0.5 and 2 sec for fluorescein and Texas red. Images were analyzed with custom software that segmented the array targets based on the DAPI image, subtracted local background, and calculated several characteristics of the signals for each target including the total intensity of each fluorochrome, the fluorescein/ Texas red intensity ratio, and the slope of the scatter plot of the fluorescein and Texas red intensities for each pixel.

Results

The procedure described here has sufficient sensitivity to allow accurate analysis of regions as small as 40 kb, approximately $10^{-5}$ of the genome, using amounts of labeled genomic DNA that are readily available from most clinical specimens. Control of repetitive sequences is sufficiently reliable that essentially any clone selected from a library can be used for a target.

Figure 1A:
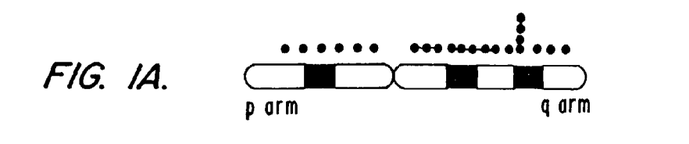
FIG. 1A shows the distribution of the physical map location on chromosome 20 of the clones disclosed here.

The target DNAs used in our measurements, the STSs or genes they contain, and their physical (FISH) map locations are listed in Table 1. FIG. 1A illustrates their distribution along chromosome 20. P1 clones are listed by number and most are available through the Resource for Molecular Cytogenetics (http:/www/rmc-www.lbl.gov). In the case of RMC20P154, a clone, RMC20P153 contains the same STS and is available from RMC. Clones chosen to detect the three previously known regions of copy number-increase were included in the array (referred to here as A1, A3, and A4), as well as additional clones designed to provide an approximately 3 Mb resolution scan of the entire chromosome. DNA for each target was dissolved in DMSO containing a small amount of nitrocellulose and water, and deposited onto amino-silane coated quartz or fused silica microscope slides using a glass capillary as described above. The inclusion of a small amount of nitrocellulose in the solution substantially increased the amount of hybridizable target DNA retained in the spots, thereby increasing signal intensities and thus sensitivity. Quadruplicate 150-300 µm diameter spots were made of each target DNA. Two hundred to 400 ng each of reference genomic DNAs, labeled respectively with fluorescein and Texas red, along with 50 µg of Cot-1 DNA to block repetitive sequences, were hybridized for 16 to 72 hours. A 1× magnification imaging system was used to acquire CCD camera images of each of the fluorochromes. Ratios for all of the spots for each target clone were averaged.

TABLE 1

| Target | Locus/Gene | FLpter |
|---|---|---|
| RMC20C177 | | 0.034 |
| RMC20P107 | CDC25B | 0.085 |
| RMC20P160 | WI-7829 | 0.158 |
| RMC20P178 | D20S186 | 0.209 |
| RMC20P005 | D20S114 | 0.272 |
| RMC20P099 | CST3 | 0.352 |
| RMC20P090 | BclX | 0.526 |
| RMC20P117 | G3/N5 | 0.548 |
| RMC20P037 | SRC | 0.603 |
| RMC20P154 | D20S44 | 0.646 |
| RMC20P058 | TOPO I | 0.675 |
| RMC20P100 | HUMSEM1 | 0.694 |
| RMC20P131 | D20S178 | 0.722 |
| RMC20P063 | PTP NR1-2 | 0.755 |
| RMC20P070 | D20S120 | 0.778 |
| B135 | | 0.806 |
| RMC20P127 | | 0.806 |
| B97 | | 0.806 |
| B130 | | 0.806 |
| RMC20P071 | D20S100 | 0.827 |
| RMC20P073 | PCK1 | 0.867 |
| RMC20C033 | | 0.906 |
| RMC20P179 | CHRNA+ | 0.948 |

The quantitative capability of our measurements was assessed by hybridizing artificial test and reference genomes containing 200 ng of total human genomic DNA spiked with varying amounts of lambda DNA, length 50 kb, to arrays containing lambda targets. This approximately simulates the behavior of targets made from human cosmid clones. The ratios were accurately proportional to copy number ratios over a dynamic range from below single copy equivalent level, 3 pg, to at least a factor of $10^3$ higher. These results indicate that processes such as reassociation of the double stranded probe fragments and non-specific binding do not significantly affect the linearity of the assay.

Figure 1B:
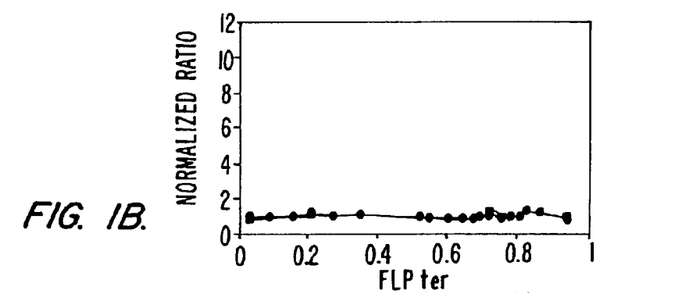
FIGS. 1B-E show copy number variation of the clones along chromosome 20 in a breast cancer cell line (BT474) and 5 breast tumors.

Two studies indicate that quantitative performance is also obtained for targets made from human genomic clones even though suppression of repetitive sequences presented additional challenges. In the first, normal male and female human genomes were compared, FIG. 1B. Ratios in each comparative hybridization were normalized so that the average of the targets on chromosome 20 was 1.0. Note that almost all are within 20% of the average. Thus ratios that fall outside of this range are likely to indicate significant copy number difference. In this study, the X chromosome target had a ratio of 0.65±0.05, demonstrating the ability to detect single copy changes in a diploid genome. The difference in this result from the expected value of 0.5 is most likely due to incomplete suppression of the repeat sequences, but the factors mentioned above may also contribute.

Figure 1C:
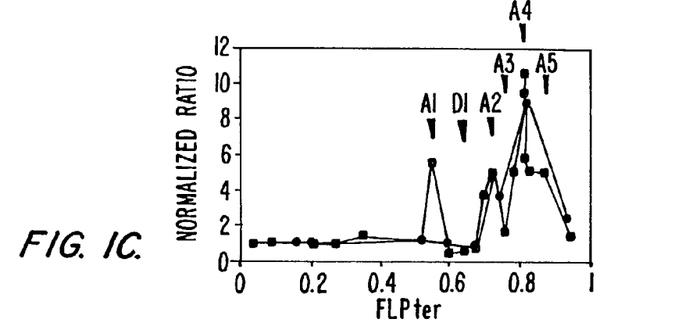

In a second study, array CGH measurements of copy number variation on chromosome 20 in the breast cancer cell line BT474 compared with previously published data obtained by FISH (FIG. 1C). While direct comparisons at identical loci cannot be made because different sets of clones were used for the two studies, the two sets of measurements are generally in excellent agreement within the ±20% uncertainty expected for these techniques. For example, the ratio of the highest peak at fractional length (FLpter) ~0.8 relative to the p arm was about 10.5 in the array measurements and ~9 with FISH. Note that the lines connecting the data points are eye guides only and do not convey information on copy number at locations between the points where measurements were made. Thus other independent regions of copy number change may be revealed, or the locations of the peaks may change somewhat, if a higher resolution array were to be used.

Figure 1D:
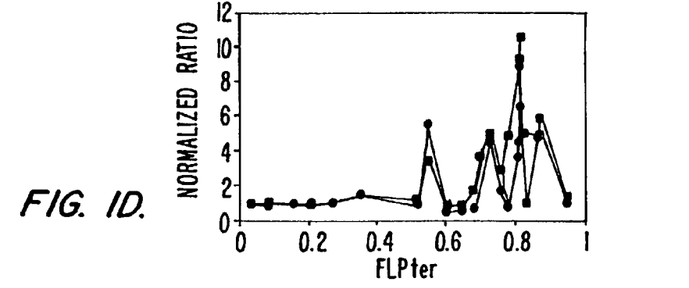
Figure 1E:
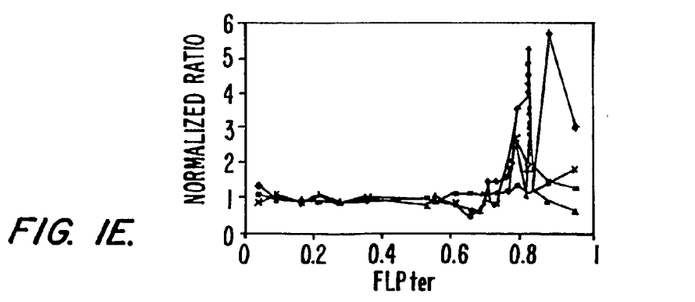
Figure 2:
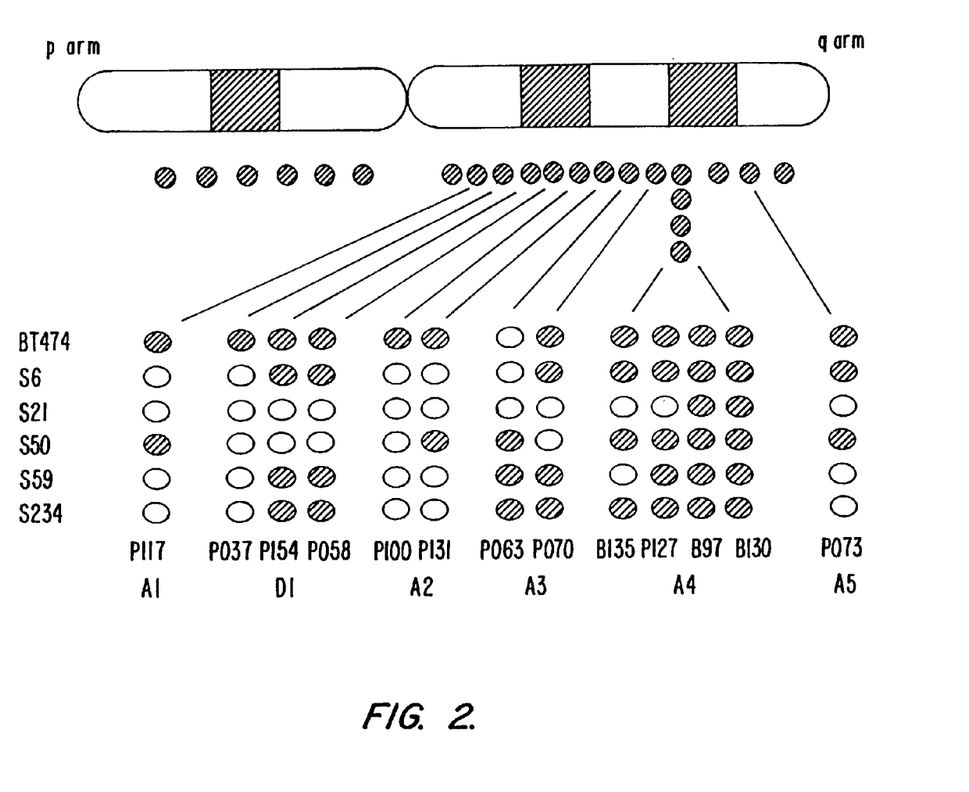
FIG. 2 summarizes the measurements of copy number increase and decrease in the regions disclosed here.
Figure 3A:
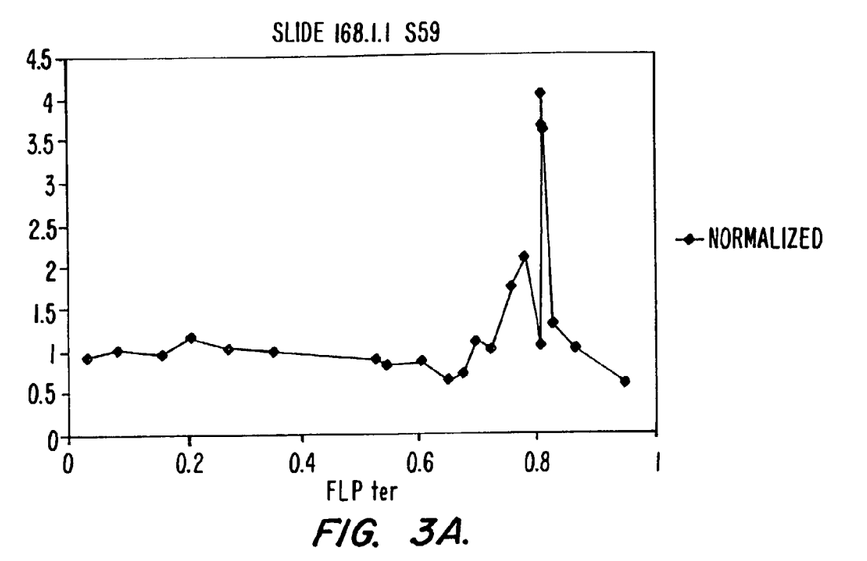
FIGS. 3A-F show individual tracings along chromosome 20 for BT474 and the 5 breast tumors studied here.
Figure 3B:
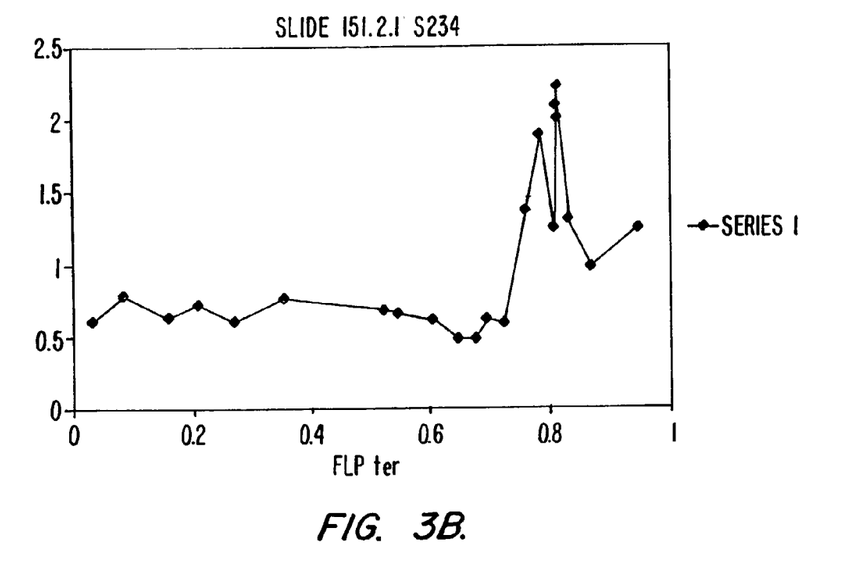
Figure 3C:
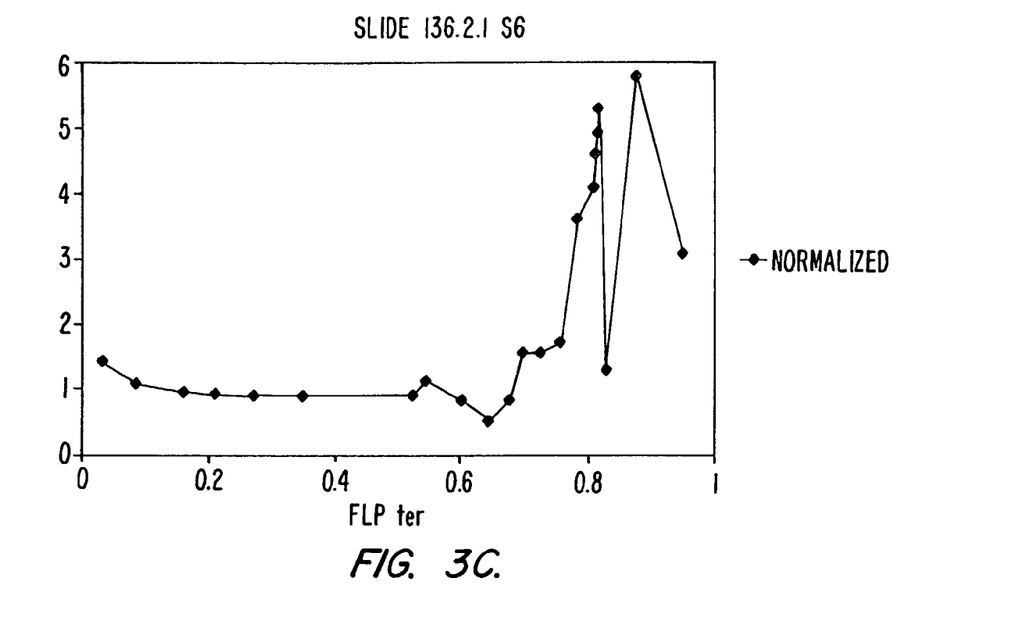
Figure 3D:
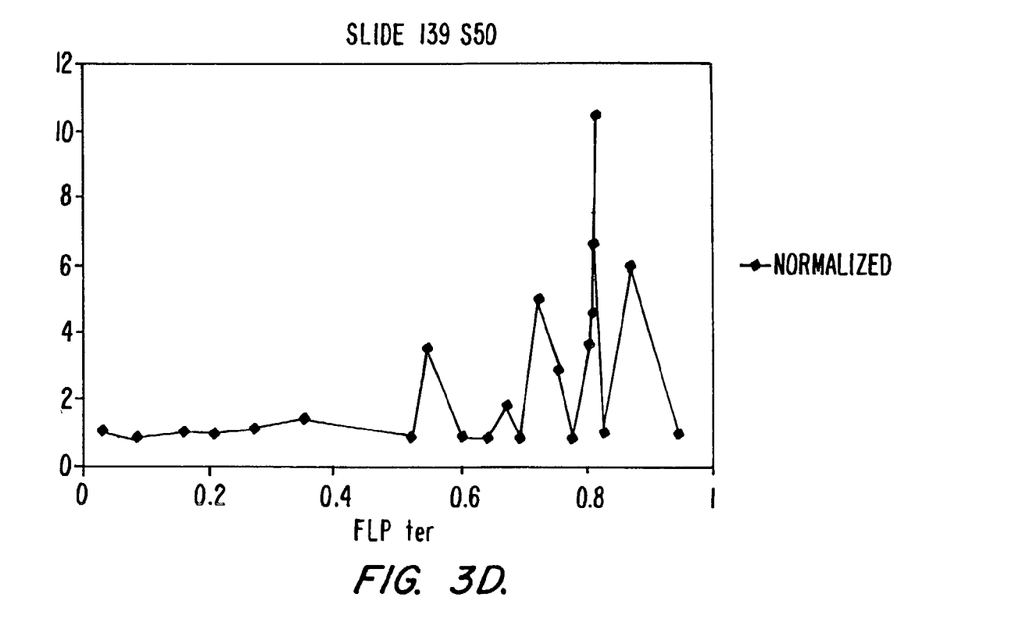
Figure 3E:
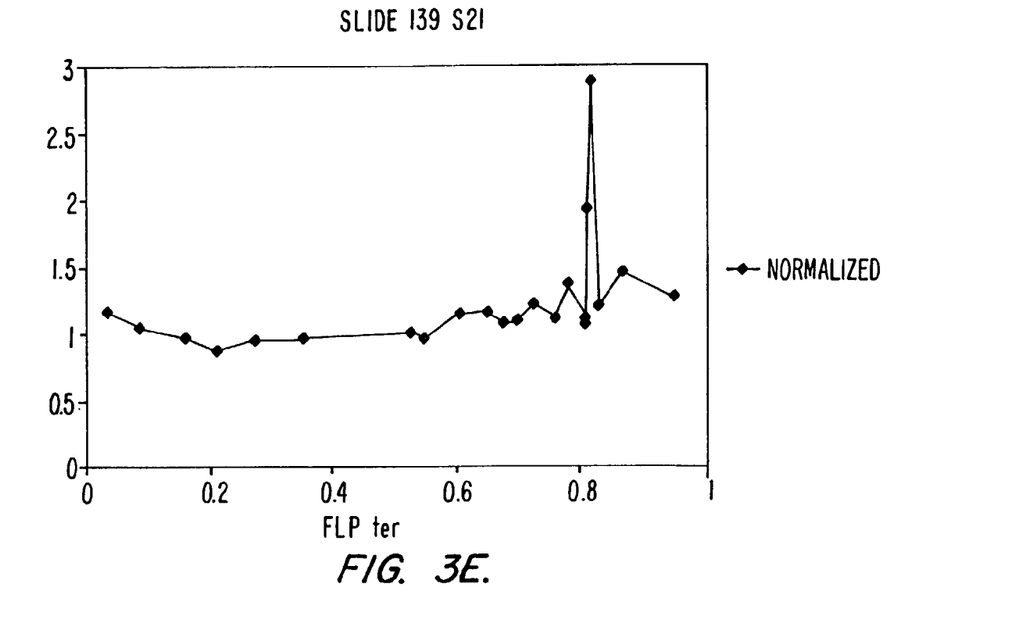
Figure 3F:
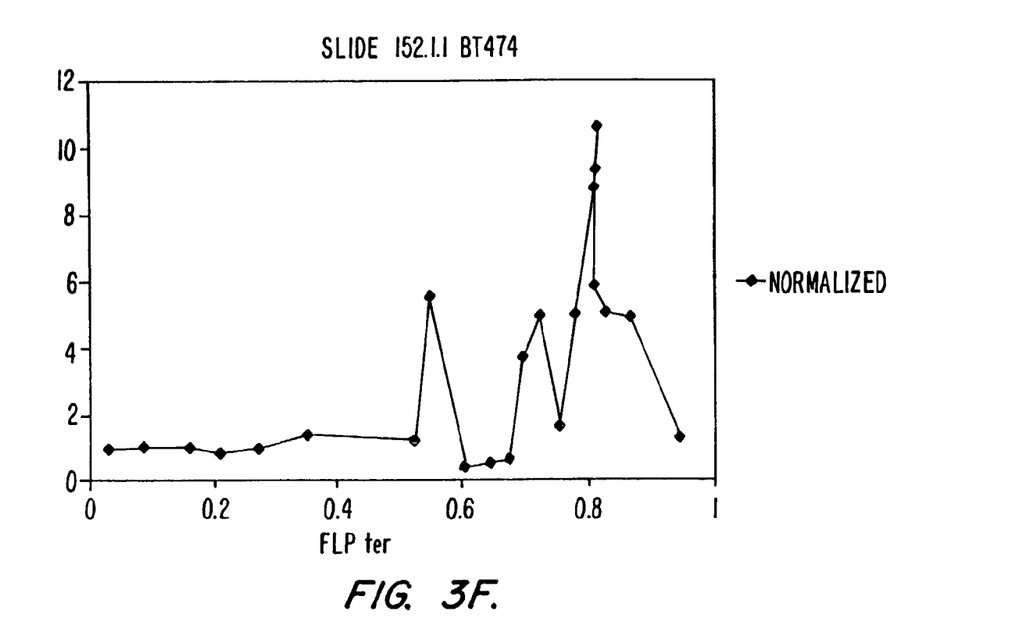

Analyses of 5 breast tumors (S-50, S-6, S-21, S-59 and S-234), obtained from the UCSF Breast Cancer SPORE, are shown in FIGS. 1D and 1E and FIG. 2. All of the ratios have been normalized so that the average ratio on chromosome 20p is 1.0. The locations of 5 regions of recurrent copy number increase, A1-A5, and one of decrease, D1, that were present in these specimens are indicated. Regions A1, A3 and A4 were previously described in breast cancer. The existence of D1, A2 and A5 was not detected in the earlier extensive studies employing conventional CGH, FISH and chromosome microdissection. The tumors in the present study were selected by FISH to have copy number increase at A4, so our results do not represent an unbiased analysis of the frequency or amplitude of these abnormalities in breast cancer. FIG. 1D compares the previously presented data from cell line BT474 to tumor S-50. The tumor contains levels of copy number increase as high as BT474 and 4 separate regions of copy number increase are apparent. A5 represents a newly discovered recurrent region of copy number change in breast cancer. It has also recently been identified by FISH in colon cancer.

FIG. 1E shows the remaining 5 tumors, which have lower level copy number increases. In one, S-21, the only copy number change found was at the selecting region A4. None have copy number increase at A1 or A2, but three have an increase at A3. Two of these, S-59 and S-234 demonstrate that A3 is a distinct, separately amplifiable region located very near A4. S6 contains the most distal amplified region, A5, also seen in tumor S-50. Three of the tumors, S6, S-59, and S-334 contained the copy number decrease D1 found in BT474. The results of all the measurements are summarized in FIG. 2 and shown in FIGS. 3A-3F.

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference.

What is claimed is:

1. A method of screening for the presence of breast cancer cells that have an increase in copy number of a target polynucleotide on chromosome 20 in a sample, the method comprising:

contacting a nucleic acid sample from a human patient with a probe which binds selectively under hybridization conditions comprising 50% formamide, 2×SSC at 37° C. and wash conditions comprising 50% formamide, 2×SSC at 45° C. for 10 minutes to a target polynucleotide sequence on a region of chromosome 20 in which copy number is altered in breast cancer cells wherein the probe binds selectively to the same target polynucleotide sequence as RMC20P100, RMC20P131, or RMC20P073, and is contacted with the sample under conditions in which the probe binds selectively with the target polynucleotide sequence to form a stable hybridization complex; and detecting the formation of a hybridization complex, thereby detecting breast cancer cells that have an increase in copy number of the target polynucleotide sequence.

2. The method of claim 1, wherein the step of detecting the hybridization complex comprises determining the copy number of the target sequence.

3. The method of claim 1, wherein the probe is labeled with digoxigenin or biotin.

4. The method of claim 1, wherein the step of detecting the hybridization complex is carried out by detecting a fluorescent label.

5. The method of claim 4, wherein the fluorescent label is FITC or Texas red.

6. The method of claim 1, wherein the sample is a tissue section.

7. The method of claim 1, wherein the sample comprises a metaphase cell.

8. The method of claim 1, wherein the sample comprises an interphase cell.

9. The method of claim 1, wherein the probe is RMC20P100.

10. The method of claim 1, wherein the probe is RMC20P131.

11. The method of claim 1, wherein the probe is RMC20P073.

12. The method of claim 1, wherein the probe binds selectively to the same target polynucleotide sequence as RMC20P100.

13. The method of claim 1, wherein the probe binds selectively to the same target polynucleotide sequence as RMC20P131.

14. The method of claim 1, wherein the probe binds selectively to the same target polynucleotide sequence as RMC20P073.

* * * * *